United States Patent
Wieland et al.

(10) Patent No.: US 11,504,129 B2
(45) Date of Patent: Nov. 22, 2022

(54) MEDICAL DEVICE INCLUDING AN ARTIFICIAL CONTRACTILE STRUCTURE

(71) Applicant: MyoPowers Medical Technologies France SAS, Besancon (FR)

(72) Inventors: Marco Wieland, Basel (CH); Claude Clement, Prilly (CH); Martin Horst, Horw (CH)

(73) Assignee: MyoPowers Medical Technologies SA, Lausanne (CH)

( * ) Notice: Subject to any disclaimer, the term of this patent is extended or adjusted under 35 U.S.C. 154(b) by 637 days.

(21) Appl. No.: 16/428,520

(22) Filed: May 31, 2019

(65) Prior Publication Data
US 2019/0282239 A1    Sep. 19, 2019

Related U.S. Application Data

(63) Continuation of application No. 15/116,694, filed as application No. PCT/EP2014/052421 on Feb. 7, 2014, now Pat. No. 10,321,912.

(51) Int. Cl.
*A61B 17/122*      (2006.01)
*A61B 17/12*       (2006.01)
(Continued)

(52) U.S. Cl.
CPC .. *A61B 17/12009* (2013.01); *A61B 17/12013* (2013.01); *A61B 17/1327* (2013.01);
(Continued)

(58) Field of Classification Search
CPC .......... A61F 2/00; A61F 2/0036; A61B 17/12; A61B 17/12009; A61B 17/1327;
(Continued)

(56) References Cited

U.S. PATENT DOCUMENTS

| | | |
|---|---|---|
| 1,728,322 A | 9/1929 | Badrian |
| 3,863,622 A | 2/1975 | Buuck |

(Continued)

FOREIGN PATENT DOCUMENTS

| | | |
|---|---|---|
| EP | 1547549 B1 | 8/2009 |
| FR | 2855744 B1 | 4/2006 |

(Continued)

*Primary Examiner* — Vi X Nguyen
(74) *Attorney, Agent, or Firm* — The Webb Law Firm

(57) ABSTRACT

A medical device has an artificial contractile structure including at least one contractile element adapted to contract a hollow body organ in such a way that said contractile element is adapted to be in a resting position or in an activated position, the activated position being defined with the contractile element constricting the hollow body organ and the resting position being defined with the contractile element not constricting the hollow body organ. The medical device further includes a tensioning device adapted to apply a force so as to tighten the contractile element around the hollow body organ, the tensioning device having a flexible transmission with a tensioning element arranged in a sheath. The sheath has an inner coiled wire coiled in a first direction, and an outer coiled wire surrounding the inner coiled wire and coiled in a second direction opposite to said first direction.

23 Claims, 10 Drawing Sheets

(51) Int. Cl.
*A61F 2/00* (2006.01)
*A61F 5/00* (2006.01)
*A61B 17/132* (2006.01)
*A61B 17/08* (2006.01)
*A61B 17/00* (2006.01)

(52) U.S. Cl.
CPC ............ *A61F 2/0036* (2013.01); *A61F 5/005* (2013.01); *A61B 17/08* (2013.01); *A61B 2017/00411* (2013.01); *A61B 2017/00477* (2013.01); *A61B 2017/00827* (2013.01); *A61B 2017/00876* (2013.01)

(58) Field of Classification Search
CPC ..... A61B 17/08; A61B 17/132; A61B 17/122; A61B 17/1227; A61B 17/1285
See application file for complete search history.

(56) References Cited

U.S. PATENT DOCUMENTS

| | | | |
|---|---|---|---|
| 4,222,377 | A | 9/1980 | Burton |
| 4,412,530 | A | 11/1983 | Burton |
| 4,878,889 | A | 11/1989 | Polyak |
| 5,554,139 | A * | 9/1996 | Okajima ............. A61M 25/005 604/528 |
| 6,074,341 | A | 6/2000 | Anderson et al. |
| 6,162,238 | A | 12/2000 | Kaplan et al. |
| 9,980,807 | B2 | 5/2018 | Lamraoui |
| 2003/0225311 | A1 | 12/2003 | Sayet et al. |
| 2004/0173219 | A1 | 9/2004 | Bakane |
| 2006/0264987 | A1 | 11/2006 | Sgro |
| 2007/0213836 | A1 | 9/2007 | Paganon |
| 2009/0264910 | A1 | 10/2009 | Laufer |
| 2010/0305397 | A1* | 12/2010 | Birk ........................ A61F 5/005 600/37 |
| 2012/0184980 | A1 | 7/2012 | Anderson et al. |
| 2012/0296157 | A1 | 11/2012 | Tozzi et al. |
| 2014/0371855 | A1* | 12/2014 | Clement ................... A61F 2/08 623/14.13 |

FOREIGN PATENT DOCUMENTS

| | | |
|---|---|---|
| WO | 2012000681 A2 | 1/2012 |
| WO | 2013091730 A1 | 6/2013 |
| WO | 2013093074 A1 | 6/2013 |
| WO | 2013165541 A1 | 11/2013 |

* cited by examiner

MEDICAL DEVICE INCLUDING AN ARTIFICIAL CONTRACTILE STRUCTURE

CROSS-REFERENCE TO RELATED APPLICATIONS

This application is a divisional of U.S. application Ser. No. 15/116,694 filed Aug. 4, 2016, which is the United States national phase of International Application No. PCT/EP2014/052421 filed Feb. 7, 2014, the disclosures of which are hereby incorporated by reference in their entirety.

BACKGROUND OF THE INVENTION

Field of the Invention

The present invention relates to the field of implantable medical devices, in particular medical devices comprising an artificial contractile structure for occluding a hollow body organ.

DESCRIPTION OF RELATED ART

In order to treat conditions such as urinary incontinence, faecal incontinence, gastro-oesophageal reflux disease and also for the treatment of obesity by gastric banding, medical devices are often implanted into the patient which comprise an artificial contractile structure, often known as a cuff, attached around a hollow body organ such as the urethra, rectum, oesophagus or the stomach. In order to reduce the diameter of the organ in question or to occlude it, the artificial contractile structure applies pressure thereto. Particularly in the case of urinary or faecal incontinence, the contractile structure essentially creates an artificial sphincter which can be opened and closed by controlling the pressure applied by the cuff.

In such applications, it is extremely important to apply this pressure as gently as possible so as to avoid damaging the organ. Currently, this is usually carried out by inflating a tube or balloon-type structure arranged on the inside of the contractile element and which applies pressure on the organ. A commercially successful example of this type of device is the AUS 800 marketed by American Medical Systems, Inc. This device and its predecessors are described in U.S. Pat. Nos. 3,863,622, 4,222,377, 4,412,530, and 4,878,889. When applied for the treatment of urinary incontinence, this device has a silicone pressure regulating balloon implanted in the perivesical space, a silicone control pump implanted in the scrotum or labia and a silicone urethral occlusive cuff wrapped around the bulbous urethra in males or the bladder neck in females. Each component may be filled with saline or radiopaque contrast media, and tubing emanating from each component may be routed between incisions for appropriate connections.

The patient operates the device by squeezing the control pump through the scrotal or labial skin, and this action transfers fluid from the cuff to the pressure regulating balloon in order to release pressure on the urethra and permit urination, after which the balloon forces fluid through a restrictor and back into the contractile element so as to re-establish an occlusive urethral pressure within 3 to 5 minutes. Furthermore, the device can be deactivated to allow tissue healing to proceed and urethral edema to subside or before inserting a catheter or other instrument into the urethra.

However, this type of device is extremely complicated to implant since three inter-operating components need to be assembled and filled with fluid in situ, and upon inflation it can fold or change its shape in a non-uniform manner, thereby creating so-called "pillows" which can cause a non-uniform pressure to be applied. Furthermore, they are prone to fluid leakage and may cause urethral atrophy and erosion. Fluid leaks may also cause complications such as post-operative infection requiring maintenance or replacement of the device.

Various attempts have been made in the past at designing non-hydraulic cuffs which do not suffer from the above limitations. For instance, U.S. Pat. No. 6,074,341 describes a medical device comprising a non-hydraulic cuff which is spring-biased in the occluded position. Tension applied to a wire member by the actuator counteracts the spring bias so as to open the cuff. Upon releasing the tension, the spring bias returns the cuff to its occluded position. This arrangement raises safety concerns, since in the case of a malfunction of the actuator the patient would not be able to urinate and would hence require immediate emergency surgery to prevent kidney damage. US 2012/0184980 describes a medical device comprising a different non-hydraulic cuff structure, in which the cuff is formed as a sheath arranged around the urethra, and wherein a tape arranged inside the sheath is attached to an actuator and is pulled so as to tighten the cuff and apply occlusive pressure to the urethra. However this cuff is complicated and bulky.

Yet further examples include US 2012/0296157, which describes medical devices comprising extremely simple wire-actuated cuffs, WO13093074, which describes soft rubber cuffs actuated by wires, and EP 1 547 549 which describes cuffs tightened by twisting a pair of wires situated inside the cuff. A gentle, uniform application of pressure to an organ does not appear to be achievable with any of these three latter examples.

An object of the invention is thus to overcome at least partially at least some of the above-mentioned drawbacks of the prior art.

SUMMARY OF THE INVENTION

The object of the invention is attained by a medical device comprising an artificial contractile structure comprising at least one contractile element adapted to contract a hollow body organ, in such a way that said contractile element is adapted to be in a resting position or in an activated position, the activated position being defined with said contractile element constricting the hollow body organ and the resting position being defined with said contractile element not constricting the hollow body organ. The medical device comprises a tensioning device adapted to apply a force so as to tighten the contractile element around said hollow body organ, the tensioning device comprising a flexible transmission comprising a tensioning element arranged in a sheath. According to the invention, said sheath comprises an inner coiled wire coiled in a first direction, and an outer coiled wire surrounding the inner coiled wire and coiled in a second direction opposite to said first direction.

Such an arrangement permits a reliable transmission of force, preventing kinking of the transmission and reducing the risk of rupture.

Advantageously, a protruding portion of the inner coiled wire may protrude from an extremity of the outer coiled wire and may be arranged such that, in an unstressed state, adjacent coils of said protruding portion are not in contact, so as to form an elastic element. This arrangement provides an integrated elastic element to force the loosening of the contractile element, keeping the number of parts low.

Advantageously, the tensioning device is arranged to cause the contractile element to apply a substantially uniform occlusive pressure of at most $8N/cm^2$, preferably at most $5N/cm^2$, further preferably at most $2N/cm^2$, said pressure varying by at most 15%, preferably by at most 10%, preferably by at most 5% around the circumference of the contact area between the contractile element and the hollow body organ when the contractile element is in its activated position.

In consequence, the medical device applies a gentle, uniform pressure to the hollow body organ, without localised pressure spikes, thereby reducing its impact on the underlying tissue, reducing damage thereto.

Advantageously, the contractile element may further comprise a flexible strip extending in a longitudinal direction, and a plurality of transversal reinforcement elements extending from a surface of the strip. These features result in a very simple, compact contractile element capable of applying the desired gentle, uniform pressure.

Advantageously, the contractile element may further comprise an elastic element arranged so as to tend to loosen the contractile element. Since such an elastic element biases the contractile element in its resting position, in the case of a failure of certain components of the medical device, the contractile element will default into its loosened position, rendering the device failsafe.

Advantageously, the tensioning device may be adapted so as to cause the flexible strip to flex into a U-shaped or U-like-shape cross-section upon application of said force, the bottom of said U-shape or U-like-shape being arranged to apply said occlusive pressure. Such a deformed shape helps to apply the pressure evenly along the circumference of the contractile element while avoiding the folds and pillows to which hydraulic cuffs can be subject.

Advantageously, at least part of the sheath being anchored to the flexible strip at a first anchoring point, the tensioning element extending from said at least part of the sheath and being anchored to the flexible strip at a second anchoring point. The tensioning element is preferably a filament, a wire, a cable or a flat strip, and may pass through at least some of the transversal reinforcement elements. A simple system for actuating the contractile element is thus proposed.

Advantageously, the tensioning device may comprise a flexible transmission comprising a tensioning element arranged in a sheath, at least part of the sheath being anchored to the flexible strip at a first anchoring point, the tensioning element extending from said at least part of the sheath and being anchored to the flexible strip at a second anchoring point. The tensioning element is preferably a filament, a wire, a cable or a flat strip, and may pass through at least some of the transversal reinforcement elements. A simple system for actuating the contractile element is thus proposed.

Advantageously, the tensioning device may comprise a release element adapted to release said occlusive pressure in response to a tension applied to said release element, said release element being preferably constituted by a further filament, a further wire, a further cable or a further flat strip.

Advantageously, the sheath may comprise two coiled wires. Preferably, it comprises said inner coiled wire coiled in said first direction, and said outer coiled wire surrounding the inner coiled wire and coiled in said second direction opposite to said first direction, which permits the reliable transmission of force, preventing kinking of the transmission and reducing the risk of rupture. Further preferably, at least one coiled wire is stretched between the first anchoring point and the second anchoring point such that, in an unstressed state, adjacent coils of the coiled wire are not in contact. In the case of a double coiled wire, typically the inner coil is stretched. The thus-stretched inner coil therefore forms the aforementioned elastic element. This arrangement eliminates the need for a separate elastic element to force open the contractile element, keeping the number of parts low.

Advantageously, the medical device may comprise an actuator separated from the contractile structure and arranged to apply a tensile force to said tensioning element, said tensioning element being attached to a connection element, such as a movable pin, protruding from a housing of said actuator, preferably by at least one of crimping, laser welding, hooking, and/or by detachable means. Simple attachment of the tensioning element to the actuator is thereby achieved.

Advantageously, the contractile element may further comprise a closure for forming the contractile element into a closed ring around a hollow body organ, the closure preferably being situated at a first extremity of the flexible strip. This closure may be arranged so as to form the contractile element into a closed loop having one of a plurality of predetermined circumferences, permitting the size of the contractile element to be set according to requirements. The closure may be arranged to be closed at one of a plurality of predetermined positions along said flexible strip, or alternatively at any convenient location.

Advantageously, the closure comprises a plurality of lips arranged to engage the flexible strip and a security device arranged to secure the lips in position. The security device may also comprise a plurality of mutually interlocking flaps serving to fix the position of the lips.

Advantageously, the medical device may further comprise means for eliminating a dead zone of said contractile element, to ensure that no force is wasted in contracting an unused section of the contractile element. These means for eliminating a dead zone may comprise a stiffener arranged to be disposed around said dead zone, or alternatively they comprise means for attaching at least part of the tensioning device to said contractile element in an adjustable position. This latter may be effected by arranging the first anchoring point to be situated proximate to said closure, and said second anchoring point to be chosen from a plurality of second anchoring points situated along the flexible strip at a plurality of distances from said first anchoring point.

Advantageously, the medical device may further comprise a magnetic latch adapted to open the contractile element in response to the application of a predetermined magnetic field. Particularly in combination with the elastic element tending to loosen the contractile element, such a magnetic latch permits to open the contractile element in case of a failure, e.g. of the actuator, such that, for instance, a urinary patient can urinate, thereby avoiding the need for emergency surgery in such a situation.

The object of the invention is also attained by a medical device comprising an artificial contractile structure comprising at least one contractile element adapted to contract a hollow body organ, in such a way that said contractile element is adapted to be in a resting position or in an activated position, the activated position being defined with said contractile element constricting the organ and the resting position being defined with said contractile element not constricting the organ, the medical device comprising a tensioning device adapted to apply a force so as to tighten the contractile element around said hollow body organ. According to the invention, the medical device comprises means for eliminating a dead zone of said contractile element in the case in which the contractile element is attached around said hollow organ with a circumference of the contractile element less than a maximum possible circumference.

In consequence, no force is wasted in contracting an unused section of the contractile element.

These means for eliminating a dead zone may advantageously comprise a stiffener arranged to be disposed around said dead zone. Alternatively, said means for eliminating a dead zone may comprise means for attaching the tensioning device to said contractile element, said means for attaching the tensioning device to said contractile element being adapted to attach at least part of the tensioning device to the contractile element in an adjustable position. In this latter case, these means for attaching the tensioning device to said contractile element may comprise a first anchoring point for attaching a first component of the tensioning device to the contractile element, said first anchoring point being situated proximate to a closure adapted to form the contractile element into a closed loop, and a second anchoring point for attaching a further component of the tensioning device to the contractile element. Said second anchoring point can be chosen from a plurality of second anchoring points situated along the contractile element at a plurality of distances from said first anchoring point, permitting to adapt the distance between anchoring points to be appropriate to the required circumference of the contractile element.

BRIEF DESCRIPTION OF THE DRAWINGS

The invention will now be further described with reference to the figures, which show.

DETAILED DESCRIPTION OF THE INVENTION

Figure 1:
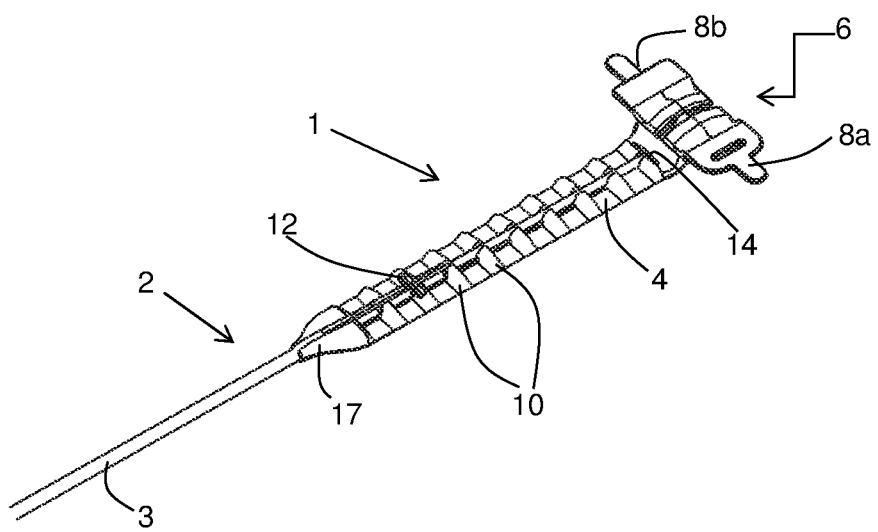
FIG. 1: a perspective view of an open contractile element according to the invention assembled with its tensioning device.
Figure 2:
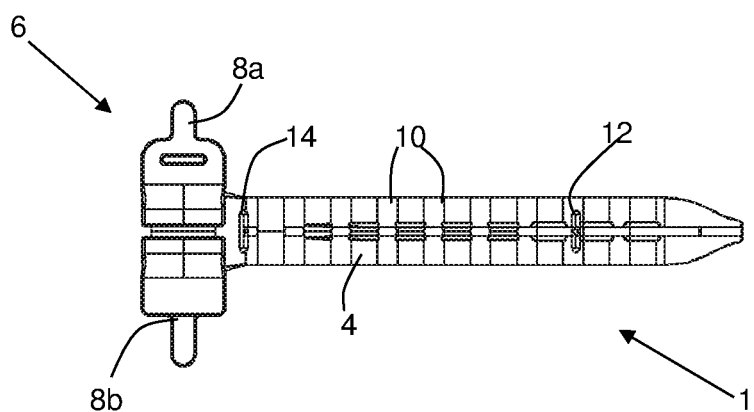
FIG. 2: a plan view of an open contractile element according to the invention.

FIG. 1 illustrates part of a medical device according to the invention, in particular a contractile element 1, otherwise known as a cuff, assembled together with a tensioning device 2. FIG. 2 illustrates contractile element 1 on its own in plan view. In the view of FIG. 1, contractile element 1 is illustrated in its open position, i.e. its position before being applied around a hollow body organ. Contractile element 1 comprises a flexible strip or ribbon 4 extending in a longitudinal direction, and constructed e.g. from implant grade silicone elastomer of sufficient Shore hardness, e.g. of between 40 and 80 Shore A, preferably between 50 and 70 Shore A. As non-limiting examples, liquid silicone elastomers from the company Nusil can be used, for instance MED-4870 with shore A hardness 70, MED-4860 with shore A hardness 60, or MED-4850 with shore A hardness 50. Alternatively, polyurethane or other flexible, biocompatible thermoplastic materials may be used instead of, or additionally to, silicone elastomer. At the distal end of flexible strip 4 is provided a closure 6 comprising a pair of mutually interlocking flaps 8a, 8b arranged so as to be able to form the contractile element 1 into a closed, substantially circular cuff around a hollow body organ by forming the flexible strip 4 into a circle and attaching the closure 6 around the flexible strip 4 at a convenient location along the flexible strip 4, as will be seen more clearly below. A plurality of transversal reinforcement elements 10 are arranged along flexible strip 4, evenly spaced and numbering 8 in the present example, however the number and the spacing can be chosen according to the needs of the skilled person. Transversal reinforcement elements 10 are straight and are aligned substantially perpendicular to the above-mentioned longitudinal direction, although other angles and other forms such as curves and crosses are also possible.

Contractile element 1 further comprises a sheath anchoring point 17 and a first anchoring point 12, arranged towards a proximal end of the flexible strip 4, and a second anchoring point 14 arranged towards the distal end of the flexible strip 4, adjacent to the closure 6. The first and second anchoring points 12, 14 serve to anchor tensioning device 2 to the contractile element 1 so as to apply a tensile force thereto, as will be described below. The sheath anchoring point 17 can be omitted if not required depending on the construction of the tensioning device 2.

Figure 3:
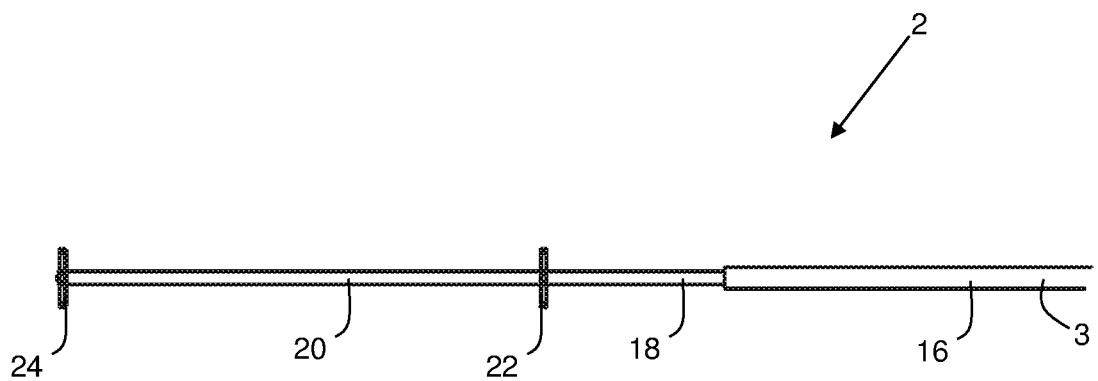
FIG. 3: a plan view of a simple form of tensioning device.

FIG. 3 illustrates a simple form of tensioning device 2. Tensioning device 2 comprises a flexible transmission 3 comprising a wire 20 surrounded by a sheath. The sheath comprises an outer sheath 16, e.g. of silicone elastomer, covering a wire coil 18, which covers the wire 20, broadly following the construction of a Bowden cable. In consequence, pulling or pushing on wire 20 will make cause it to move with respect to the sheath. The wire 20 may be e.g. of stainless steel or other metal alloys (e.g. SS 304V, 316L, MP35N, MP35NLT), and may be housed in or coated with an ePTFE or PTFE tube or coating to reduce friction. Additionally, the number and diameter of the strands composing the wire 20 should be chosen to minimise friction, and the wire may also be redrawn so as to make its surface smooth. Alternatively, the wire 20 may be made of titanium, Nitinol, or any other convenient biocompatible metal, or a polymer such as PTFE, Aramid, ultra high molecular weight polyethylene (e.g. as sold by Dyneema), or similar. Wire 20 may also be flat or oval in cross-section, and may even be of variable cross-section, e.g. circular within the wire coil 18, and flat within the contractile element 1. Alternatively, a cable, of either circular or flat cross-section, could be used instead of the wire.

Outer sheath 16 is attached to the contractile element 1 at sheath anchoring point 17 (see FIG. 1). A first anchor 22 arranged to engage with first anchor point 12 is attached to the wire coil 18, and the wire 20 is free to slide through an opening therein. A second anchor 24 arranged to engage with second anchor point 14 is attached to wire 20. The anchors 22, 24 may be glued into the corresponding anchor points 12, 14. The opposite end of tensioning device 2 is arranged to be attached to an appropriate actuator, such as that described in WO13091730, WO13093074 or WO12000681, herein incorporated by reference in their entirety. A force applied by the actuator to wire 20 causes it to slide within wire coil 18 so as to reduce the separation of first anchor 22 and second anchor 24.

Figure 4:
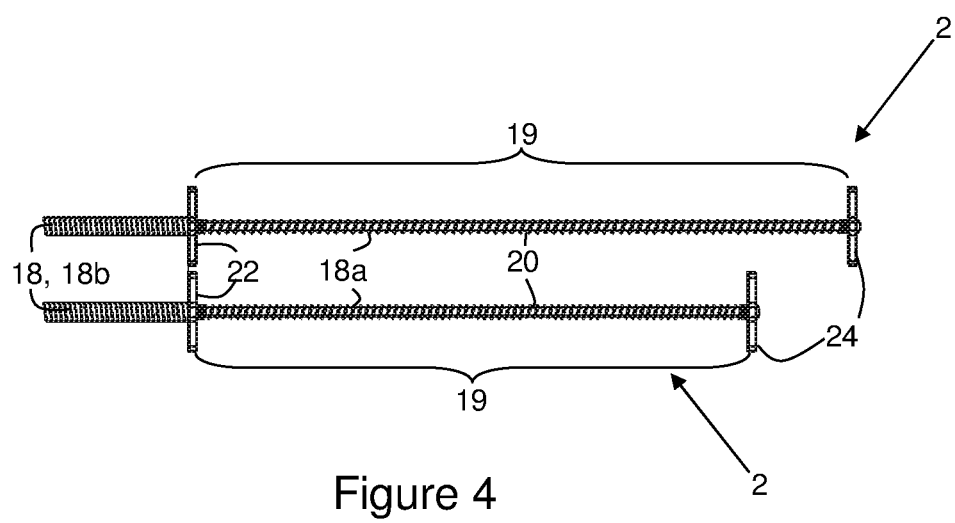
FIG. 4: plan views of an embodiment of tensioning device, in an inactive, extended position (top) and in an active, contracted position (bottom)
Figure 5A:
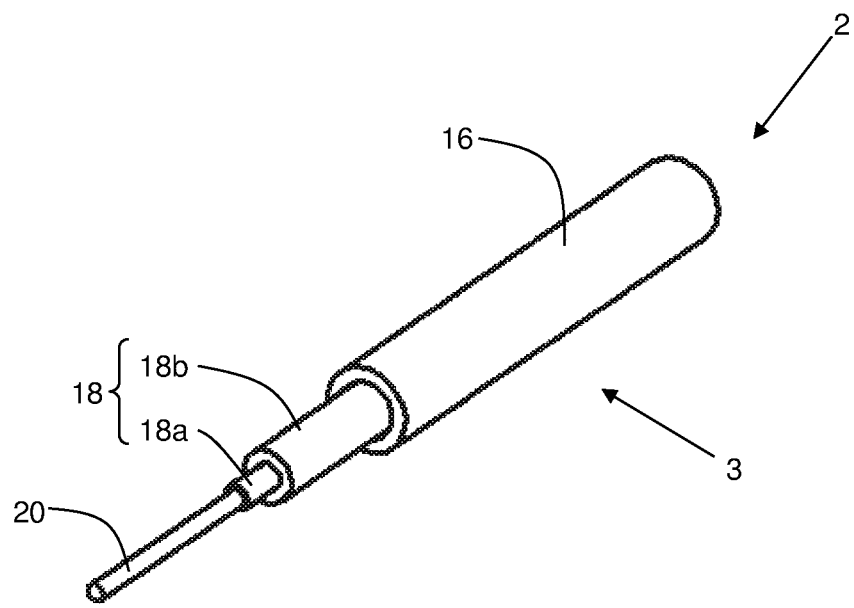
FIG. 5a: a perspective view of the global arrangement of the flexible transmission.
Figure 5B:
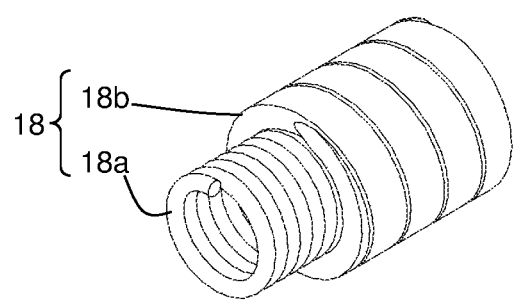
FIG. 5b: a perspective view of the arrangement of the double-coiled sheath.

FIG. 4 illustrates a particularly advantageous embodiment of tensioning device 2, in an inactive, extended position (top) and in an active, contracted position (bottom). Note that outer sheath 16 has not been represented in this figure. In this embodiment, wire coil 18 is formed as a double wire coil as illustrated in FIG. 5a (showing the global arrangement of flexible transmission 3 comprising wire 20, wire coils 18a, 18b and outer sheath 16) and 5b (showing in detail the arrangement of wire coils 18a and 18b alone), in which can clearly be seen an inner wire coil 18a wound in a first direction around wire 20, and an outer wire coil 18b surrounding the inner wire coil 18a, wound in a second direction opposite to the first direction. Such a double-coil arrangement helps to prevent kinking of the transmission portion of the tensioning device 2 and helps reduce the risk of rupture. In this embodiment, outer wire coil 18b and optionally also inner wire coil 18a are attached to first anchor 22, where outer wire coil 18b terminates. Inner wire coil 18a continues to second anchor point 24, and this section of inner wire coil 18a is pre-stretched with a permanent set, i.e. a permanent plastic deformation, so that adjacent coils of inner wire coil 18a do not touch in the inactive, i.e. open, state of the tensioning device 2. As a result, the pre-stretched section 19 of inner coil 18a acts as a spring tending to force the anchors 22, 24 apart and hence to urge the tensioning device 2 into its inactive, i.e. open, position as illustrated in the upper part of FIG. 4. Furthermore, the pre-stretched section 19 of inner coil 18a serves to limit the maximum amount of force which can be applied to contractile element 1 since second anchor 24 cannot approach first anchor 22 closer than the point at which the pre-stretched section 19 of inner coil 18a becomes coil bound, i.e. the point at which adjacent coils enter into contact with each other. Alternatively, a separate spring of any convenient configuration (such as a helical spring acting to push the anchors 22, 24 apart, or a leaf spring tending to straighten the contractile element 1) may be utilised to force the opening of the contractile element 1, the pre-stretched section 19 of inner wire coil 18a not be necessary in such a case.

Furthermore, as a simpler alternative, wire coil 18 may be formed as a single coil, this single coil being provided with a pre-stretched section 19 so as to form a spring in exactly the same manner as in the example of FIG. 4. Further alternatively, a multi-layer coil comprising more than two coils can be used.

An alternate arrangement of tensioning device 2, not illustrated, incorporates a pair of wires 20 arranged so as to operate in opposite directions, such that pulling on a first wire tightens the contractile element 1, whereas pulling on the second wire loosens the contractile element 1.

Figure 6:
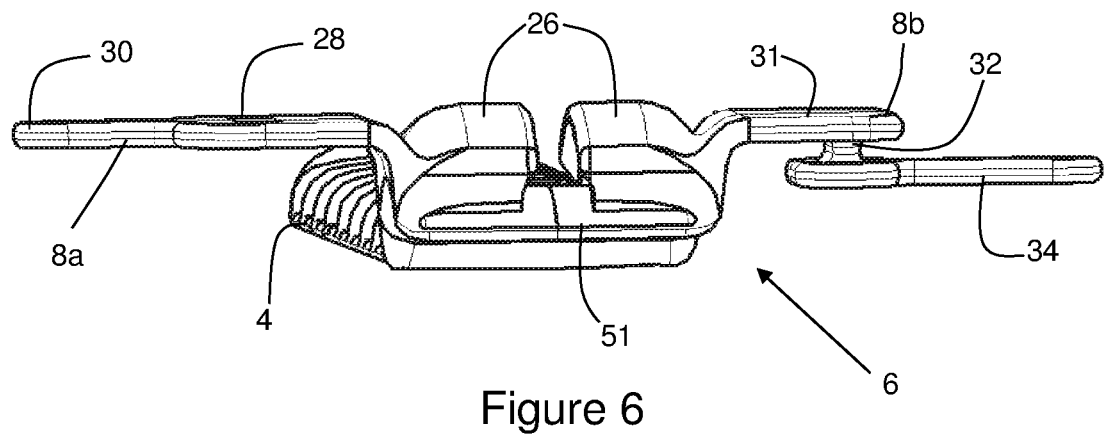
FIG. 6: a perspective view of the arrangement of the closure situated at the distal end of the flexible strip.

FIG. 6 illustrates in detail the arrangement of closure 6 situated at the distal end of flexible strip 4. Closure 6 comprises a pair of flexible lips 26 overhanging a transverse connecting member 51 and extending towards each other from the edges of flexible strip 4 and adapted to embrace flexible strip 4, together with one or more transversal reinforcement elements 10, so as to form a closed cuff of a convenient circumference. Closure 6 may be applied at one of a plurality of discrete positions along flexible strip 4, or alternatively at any convenient point therealong depending on the exact design of the closure 6. For instance, if the lips 26 are provided on their inside face with a groove conforming to a transversal reinforcement element 10, the lips will embrace the flexible strip 4 and a transversal reinforcement element 10, and help to prevent slipping of the closure 6 along the flexible strip 4.

To ensure that the cuff is securely closed and cannot slip under normal operational forces applied thereto, i.e. up to at least 4 N of applied force, a security device comprising a pair of mutually interlocking flaps 8a and 8b are provided, each adjacent to one of the lips 26. In the present example, flap 8a comprises an opening 28 and the tab 30 which can be gripped by a surgeon so as to close the cuff. Flap 8b, on the other hand, is provided with a root portion 31 adjacent to the corresponding lip 26, a connecting element 32 connecting the root portion 31 to a further tab 34, situated in a different plane to the root portion 31. Upon closing the closure 6, further tab 34 is passed through opening 28 and pulled tight such that connecting elements 32 passes through the opening 28, and the tabs point in opposite directions, as clearly visible on FIGS. 7 and 8.

Figure 7:
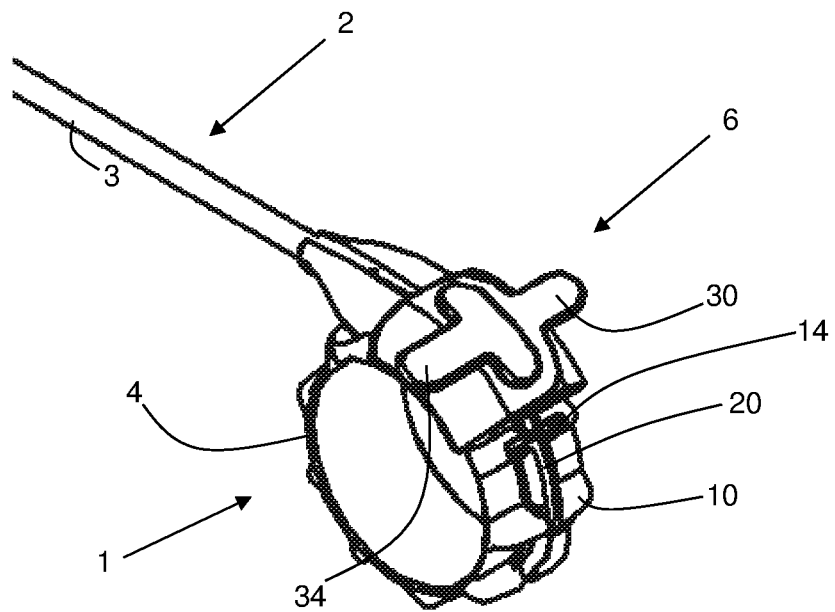
FIG. 7: a perspective view of a contractile element closed and formed into a substantially annular cuff.

FIG. 7 illustrates contractile element 1 closed and formed into a substantially annular cuff. Flexible strip 4 has been turned back on itself and closure 6 has been utilised to secure the contractile element 1 in its closed position, shown here at its maximum circumference, which may be for instance 6 cm for implanting around a male urethra, or 11 cm for implanting around the bladder neck in females. However, other maximum circumferences are of course possible. As an example, the width of the flexible strip 4 may be between 7 and 10 mm, however naturally larger and smaller widths are likewise possible. The closure 6 may be arranged so as to be closed at a number of discrete closing positions, or alternatively may be arranged so that it can be closed at any convenient point along the flexible strip 4.

Figure 8:
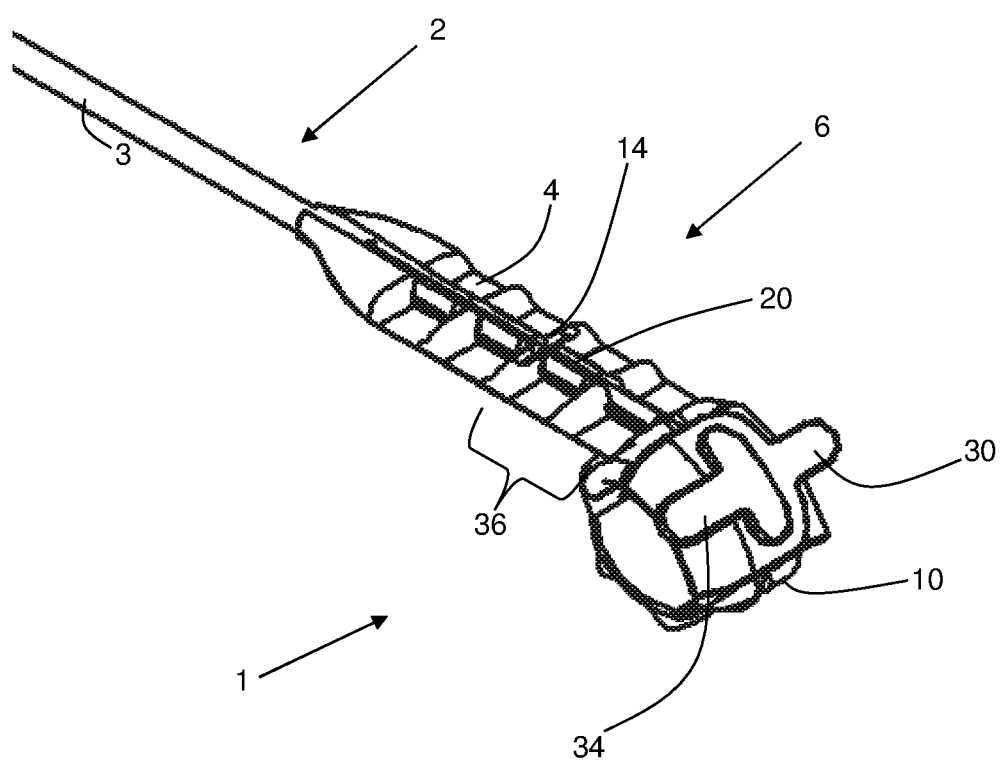
FIG. 8: a perspective view of a contractile element closed and formed into a substantially annular cuff of lesser circumference.

FIG. 8 shows, in a manner similar to FIG. 7, contractile element 1 formed into a substantially annular cuff of smaller circumference, shown here at its minimum circumference which may be e.g. 3 cm for male urethras and 6 cm for females bladder necks. Again, other minimum circumferences are likewise possible. To do this, the flexible strip 4 is turned back on itself and closure 6 is closed around an appropriate part of the flexible strip 4. It should be noted that in this configuration a portion of the contractile element 36 situated between the first anchor point 14 and the closure 6 will be put under tension by tensioning device 2, but does not contribute to applying pressure to the hollow body organ around which the contractile element 1 is attached.

Figure 9:
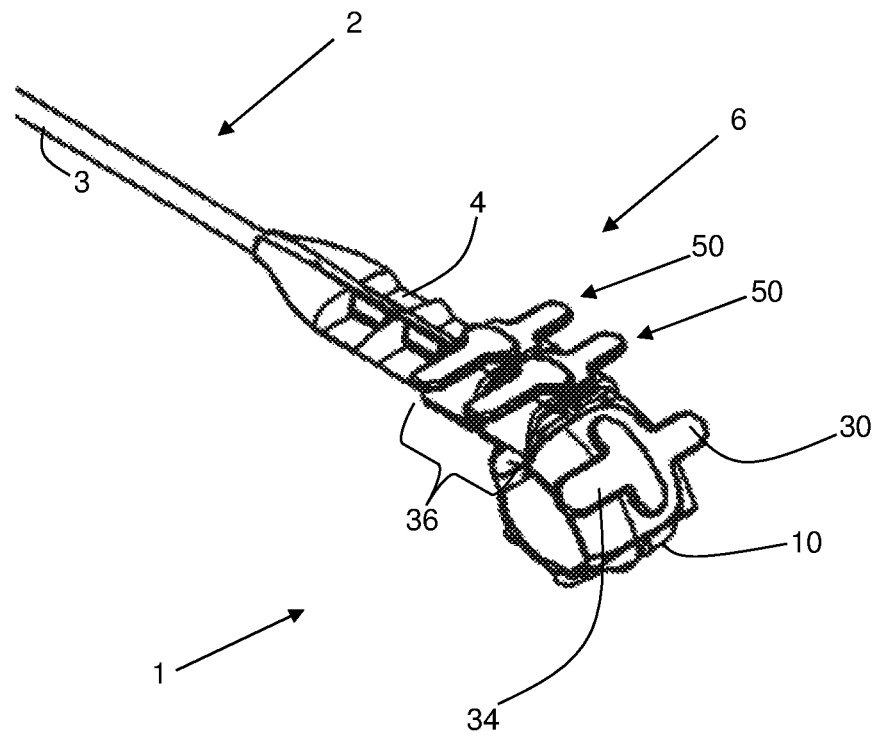
FIG. 9: a perspective view of a contractile element closed and formed into a substantially annular cuff of lesser circumference and provided with stiffening elements.
Figure 10A:
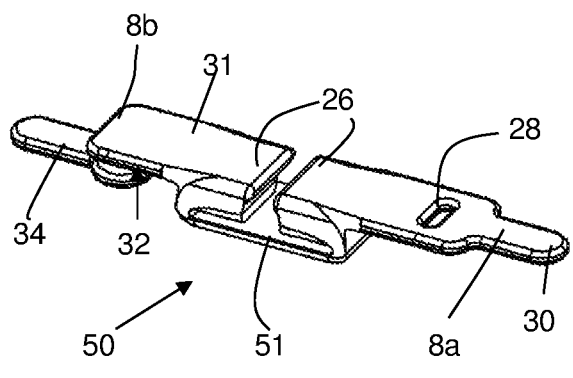
FIGS. 10a, 10b: perspective views of a stiffening element respectively in its open and closed states.
Figure 10B:
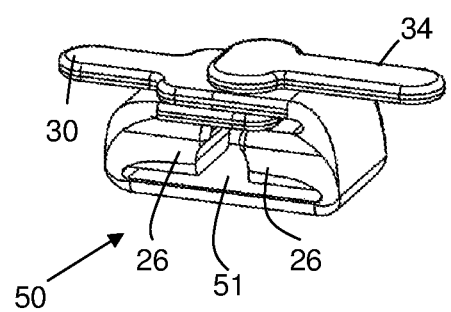

This portion 36 is referred to as a "dead zone", and its impact can be minimised e.g. by adding a stiffener 50 around the dead zone 36 after closure of the contractile element 1, as illustrated in FIG. 9. The stiffeners 50 as illustrated are formed similarly to closure 6 and comprise a corresponding safety device comprising flaps 8a and 8b, and are illustrated in more detail in FIG. 10a in an open state and in FIG. 10b in a closed state. The same reference signs used in respect of the closure 6 (see FIG. 6) are used in FIGS. 10a and 10b, and the description of each component is the same mutatis mutandis and need not be repeated here. The lips 26 may comprise a groove conforming to the shape of a transversal reinforcement element 10, or may be groove-free and sized to fit between two adjacent transversal reinforcement elements 10. Such a stiffener assures that the force applied to the contractile element 1 is not wasted on actuating a part of the cuff which does not apply force to the hollow body organ.

Alternatively, in a non-illustrated variant, such a stiffener, if required, may comprise a hollow tube applied around part of tensioning device 2 upon assembly and then, after forming the cuff around a hollow body organ, the stiffener can be slid over the dead zone 36 and secured in place e.g. with a suitable clip or clamp. Other forms of stiffener are naturally possible.

Alternatively, a further non-illustrated construction in which a dead zone can be avoided is to arrange the closure 6 on the proximal end of flexible strip 4, and to arrange a plurality of second anchor points 14 such that the second anchor 24 can be set in an adjustable position. Any excess material of the flexible strip 4 will thus overhang past the closure 6 and can be trimmed off if required since it does not contain any part of the tensioning device 2.

Figure 11A:
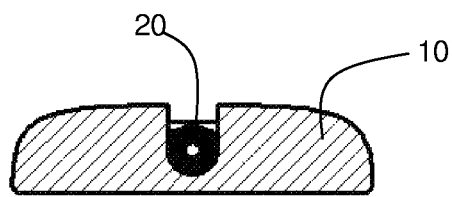
FIGS. 11a-d: various cross-sections through a contractile element in its resting and actuated positions.
Figure 11C:
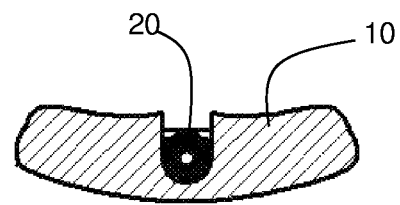
Figure 11B:
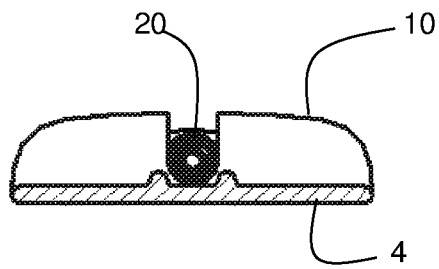

FIGS. 11a and 11b illustrate the cross-sectional shape of the contractile element 1 in its applied but resting position, i.e. contractile element 1 has been formed into an annular cuff but no force has been applied by the tensioning device 2. FIG. 11a illustrates the cross-sectional shape of a transversal reinforcement element 10 and FIG. 11b shows the cross-sectional shape of flexible strip 4 between two transversal reinforcement elements 10. In each case, the transversal reinforcement elements 10 in question are situated between the two anchor points 12, 14. As can clearly be seen, the cross-sectional shape of the contractile element 1 is substantially flat, and therefore applies little or no pressure to the hollow body organ around which it is closed.

Figure 11D:
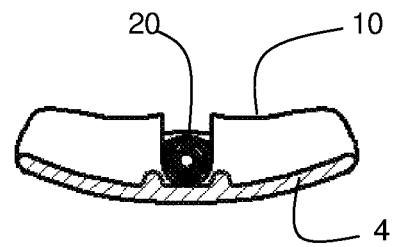

FIGS. 11c and 11d illustrate the cross-sectional shape of the contractile element 1 at positions corresponding to those of FIGS. 11a and 11b respectively when the tensioning device 2 applies a tensile force to the contractile element 1, i.e. when the contractile element 1 is in its activated position. In contrast to the prior art cuffs referenced above, the contractile element 1 is not merely tightened by reducing its circumference in the manner of a slipknot or by twisting wires together. When a tensile force is applied by tensioning device 2, second anchor 24 is pulled towards first anchor 22, tightening the wire 20 down on the flexible strip 4. This causes the contractile element 1 to flex, the transversal reinforcement elements 10 resisting this flexion and causing the contractile element 1 to curve gently in its cross-section broadly into a U-shape or U-like-shape rather than the aggressive V-shape that would be taken by the cross-section of the contractile element 1 in the case in which the transversal reinforcement elements were not present. In consequence, a gentle pressure is applied to the hollow body organ over as large an area as possible, reducing tissue damage.

As a result, the contractile element 1 cannot pinch underlying tissue, and applies a pressure of at most 8N/cm2, preferably at most 5N/cm2, further preferably at most 2N/cm2. Furthermore, due to the way in which the flexible strip 4 deforms to apply pressure, this pressure is particularly uniform around the circumference of the flexible strip, and varies by at most 15%, preferably by at most 10%, preferably by at most 5% along the flexible strip 4 where it is in contact with the hollow body organ when the contractile element 1 is activated.

Figure 12:
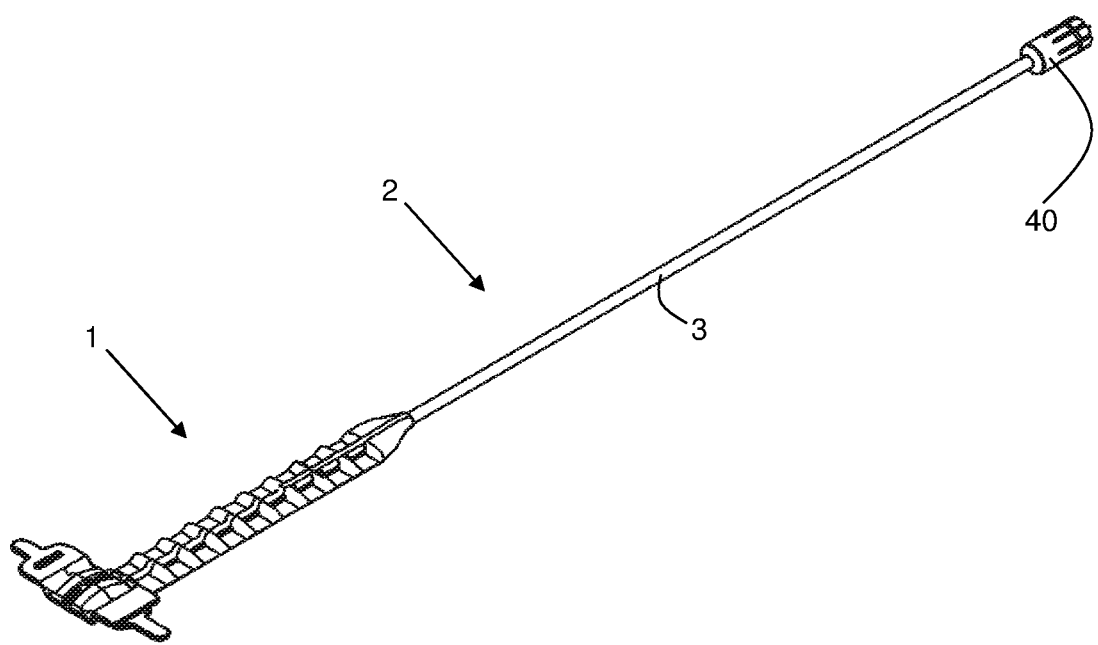
FIG. 12: a perspective view of a contractile element assembled with a tensioning device, ready for implantation.

FIG. 12 illustrates a contractile element 1 assembled with a tensioning device 2, ready for implantation. Although tensioning device 2 can be attached to an actuator (not illustrated) by any convenient means such as crimping, laser welding, clamping or so on of the various components of the transmission 3, the assembly illustrated in FIG. 10 advantageously comprises a connector 40 for attachment to a corresponding connector on the actuator. Connector 40 may be e.g. a quick-release type connector of any convenient configuration.

The actuator 60 (see FIG. 13) with which the contractile element 1 is used may be an actuator corresponding to those disclosed in any of the documents WO13091730, WO13093074 or WO12000681, or any other convenient actuator. Furthermore, the medical device according to the invention may comprise two or more contractile elements 1 as described herein, e.g. arranged in pairs similarly to the arrangement disclosed in WO13091730 and WO13093074, each of the contractile elements being operated alternately so as to allow the underlying tissue to recover.

Figure 13:
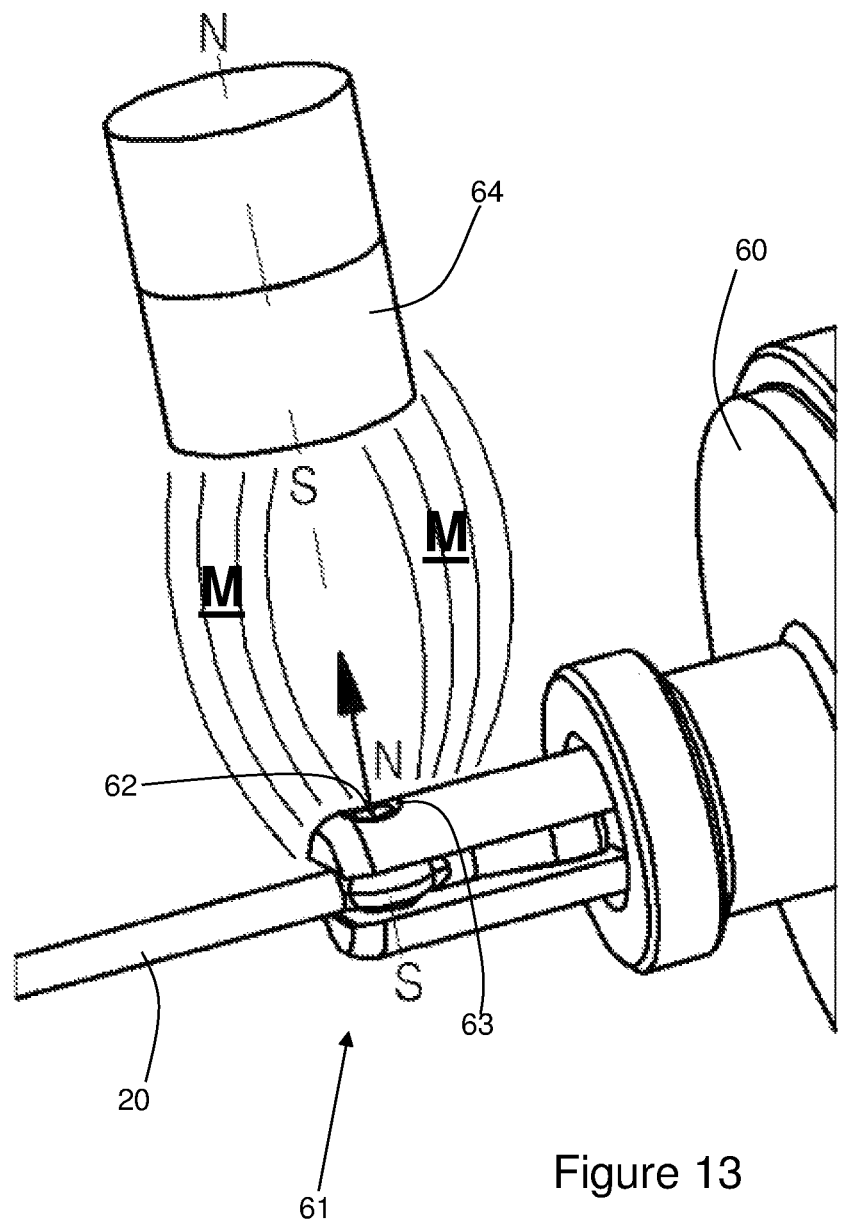
FIG. 13: a perspective view of a magnetic latch arrangement.

As shown in FIG. 13, as a further safety measure, the actuator 60 may be arranged such that the application of a strong magnetic field M causes a release of tension on the cuff. In the illustrated embodiment, the coupling 61 between the wire 20 of the tensioning device 3 and the actuator 60, can be constructed as a magnetic latch, comprising a magnetic pin 62 arranged in a housing 63 such that the application of a strong magnetic field M causes the magnetic pin 62 to be at least partially withdrawn from its housing 63 towards the source 64 of the magnetic field M, e.g. a strong permanent magnet or electromagnet. This causes the wire 20 to separate from the actuator 60, causing these two components to separate. Ideally, the pin 62 is captive. Since the tensioning device 2 is biased towards opening the cuff due to the pre-stretched section 19 of inner coil 18a or the alternative auxiliary spring, the cuff will then open and no longer occlude the hollow body organ in the case of a malfunction of the actuator with the cuff in its closed state. In the case of treatment of urinary incontinence, this would prevent the bladder filling up with urine and damaging the kidneys and would thus obviate the need for emergency surgery, although surgery may be required to remedy the fault and put the medical device back in its operative state.

Figure 14A:
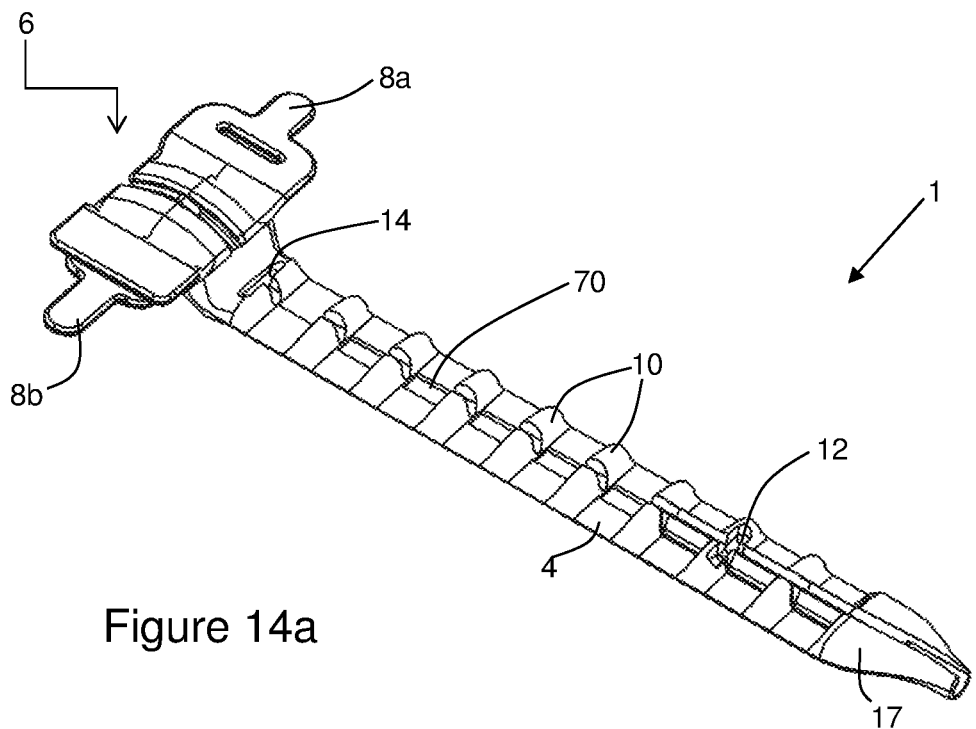
FIGS. 14a, 14b: a perspective and a plan view respectively of a variant of a contractile element, in its open position.
Figure 14B:
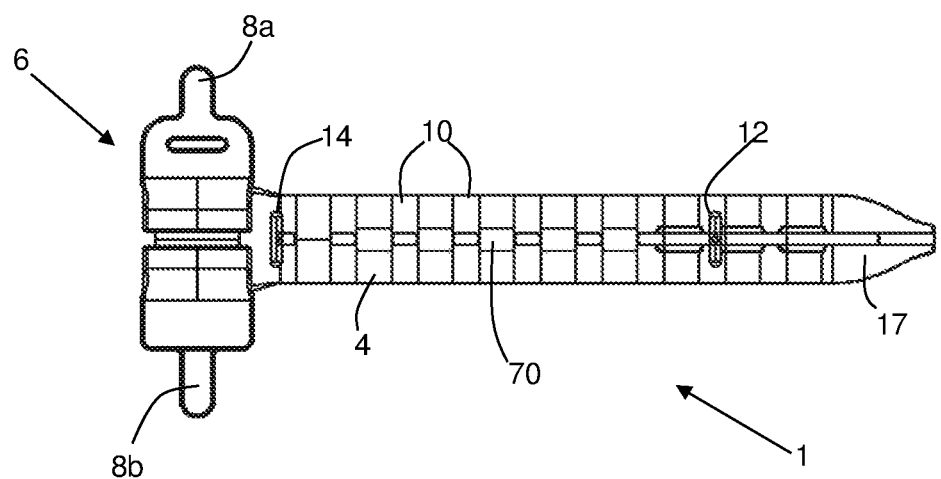

FIGS. 14a and 14b illustrate in perspective and plan views a variant of contractile element 1, in which the same reference signs have been used to indicate the same parts. The variant of contractile element 1 of FIGS. 14a and 14b differs from that of the foregoing in that the flexible strip 4 is provided with openings 70 situated between pairs of adjacent transversal reinforcement elements 10. In the present example, these openings 70 are formed as slots between some of the transversal reinforcing elements 10. As illustrated, five interstices between the transversal reinforcing elements 10 are provided with openings 70, however the number and position of the openings 70 can be chosen at will. These openings 70 of generally rectangular form are disposed on the centreline of the contractile element 1 and extend towards its edges. Other forms of openings 70 are of course possible. The openings serve to reduce the tensile force required to apply force to the hollow body organ, since less contractile element material needs to be compressed when the contractile element 1 is actuated.

The invention claimed is:

1. A medical device comprising:
   an artificial contractile structure comprising at least one contractile element adapted to contract a hollow body organ, such that said contractile element is adapted to be in a resting position or in an activated position, the activated position being defined with said contractile element constricting the hollow body organ and the resting position being defined with said contractile element not constricting the hollow body organ,
   a tensioning device adapted to apply a force so as to tighten the contractile element around said hollow body organ, the tensioning device comprising a flexible transmission comprising a tensioning element arranged in a sheath,
   wherein said sheath comprises an inner coiled wire coiled in a first direction, and an outer coiled wire surrounding the inner coiled wire and coiled in a second direction opposite to said first direction.

2. The medical device according to claim 1, wherein a protruding portion of the inner coiled wire protrudes from an extremity of the outer coiled wire and is arranged such that, in an unstressed state, adjacent coils of said protruding portion are not in contact, so as to form an elastic element.

3. The medical device according to claim 1, wherein said tensioning device is arranged to cause the contractile element to apply a substantially uniform occlusive pressure of at most 8N/cm², said pressure varying by at most 15% along the circumference of the contact area between the contractile element and the hollow body organ when the contractile element is in its activated position.

4. The medical device according to claim 1, wherein the contractile element further comprises:
   a flexible strip extending in a longitudinal direction;
   a plurality of transversal reinforcement elements extending from a surface of the flexible strip.

5. The medical device according to claim 4, wherein the tensioning device is adapted so as to cause the flexible strip to flex into a U-shaped cross-section upon application of said force, the bottom of said U-shape being arranged to apply said occlusive pressure.

6. The medical device according to claim 4, wherein the flexible strip comprises a plurality of openings, each opening being situated between two adjacent transversal reinforcement elements.

7. The medical device according to claim 4, wherein at least part of the sheath being anchored to the flexible strip at a first anchoring point, the tensioning element extending from said at least part of the sheath and being anchored to the flexible strip at a second anchoring point.

8. The medical device according to claim 7, wherein said inner coiled wire is stretched between the first anchoring point and the second anchoring point such that, in an unstressed state, said adjacent coils of said inner coiled wire are not in contact, so as to form the said elastic element.

9. The medical device according to claim 7, wherein said first anchoring point is situated proximate to said closure, and said second anchoring point can be chosen from a plurality of second anchoring points situated along a flexible strip at a plurality of distances from said first anchoring point.

10. The medical device according to claim 4, wherein the tensioning element passes through at least some of the transversal reinforcement elements.

11. The medical device according to claim 4, wherein the contractile element further comprises a closure for forming the contractile element into a closed loop around a hollow body organ, the closure being situated at a first extremity of the flexible strip.

12. The medical device according to claim 11, wherein the closure is arranged so as to form the contractile element into a closed loop having one of a plurality of predetermined circumferences.

13. The medical device according to claim 11, wherein the closure is arranged to be closed at one of a plurality of predetermined positions a flexible strip.

14. The medical device according to claim 11, wherein the closure comprises a plurality of lips arranged to engage a flexible strip and a security device arranged to secure the lips in position.

15. The medical device according to claim 14, wherein the security device comprises a plurality of mutually interlocking flaps.

16. The medical device according to claim 1, wherein the contractile element further comprises an elastic element arranged so as to tend to loosen the contractile element.

17. The medical device according to claim 1, wherein the tensioning element is a filament, a wire, a cable or a flat strip.

18. The medical device according to claim 17, wherein said tensioning device comprises a release element adapted to release said occlusive pressure in response to a tension applied to said release element, said release element being preferably constituted by a second filament, a second wire, a further cable or a second flat strip.

19. The medical device according to claim 1, further comprising an actuator separated from the contractile element and arranged to apply a tensile force to said tensioning element, said tensioning element being attached to a connection element, such as a movable pin, protruding from a housing of said actuator, by at least one of crimping, laser welding, hooking, and detachable means.

20. The medical device according to claim 1, further comprising means for eliminating a dead zone of said contractile element.

21. The medical device according to claim 20, wherein said means for eliminating a dead zone comprise a stiffener arranged to be disposed around at least part of said dead zone.

22. The medical device according to claim 20, wherein said means for eliminating a dead zone of said contractile element comprise means for attaching at least part of the tensioning device to said contractile element in an adjustable position.

23. The medical device according to claim 1, further comprising a magnetic latch adapted to open the contractile element in response to the application of a predetermined magnetic field.

* * * * *